US009895511B2

(12) United States Patent
Rasmussen

(10) Patent No.: US 9,895,511 B2
(45) Date of Patent: Feb. 20, 2018

(54) INTRODUCER ASSEMBLY AND PROTECTIVE SLEEVE THEREFOR

(71) Applicant: COOK MEDICAL TECHNOLOGIES LLC, Bloomington, IN (US)

(72) Inventor: Erik E. Rasmussen, Slagelse (DK)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 201 days.

(21) Appl. No.: 14/676,416

(22) Filed: Apr. 1, 2015

(65) Prior Publication Data

US 2015/0290426 A1 Oct. 15, 2015

(30) Foreign Application Priority Data

Apr. 10, 2014 (GB) .................................. 1406501.5

(51) Int. Cl.
*A61M 25/00* (2006.01)
*A61F 2/962* (2013.01)
*A61M 25/06* (2006.01)

(52) U.S. Cl.
CPC ......... *A61M 25/0045* (2013.01); *A61F 2/962* (2013.01); *A61M 25/005* (2013.01);
(Continued)

(58) Field of Classification Search
CPC ............ A61M 25/0045; A61M 25/005; A61M 25/0053; A61M 2025/0046;
(Continued)

(56) References Cited

U.S. PATENT DOCUMENTS 4,790,817 A 12/1988 Luther
5,454,795 A * 10/1995 Samson ................ A61L 29/041
600/435
(Continued)

FOREIGN PATENT DOCUMENTS

EP 0330012 8/1989
EP 1 415 671 5/2004
(Continued)

OTHER PUBLICATIONS

Search and Examination Report for GB Application No. 1406501.5 dated May 26, 2015, 6 pages.
(Continued)

*Primary Examiner* — Bradley Osinski
(74) *Attorney, Agent, or Firm* — Brinks Gilson & Lione

(57) ABSTRACT

An introducer assembly includes an introducer element (80), which may have a catheter or sheath (82), a pusher element (84) holding an implantable medical device (88) and a dilator tip (90). The assembly also includes a protective sleeve (72) within which the introducer element (80) is disposed. The protective sleeve (72) is made of an absorbable hydrophilic material which is deployed in a wetted condition and acts as a cushion or barrier between the introducer element (80) and the vessel wall (60). The sleeve can prevent trauma to the vessel during the deployment of the introducer element (80) and as a result can avoid vessel spasm which can occur in delicate vessels such as the cerebral vessels. The introducer assembly may be used for cerebral applications.

21 Claims, 3 Drawing Sheets

(52) U.S. Cl.
CPC . *A61M 25/0053* (2013.01); *A61F 2210/0004* (2013.01); *A61M 2025/0004* (2013.01); *A61M 2025/0042* (2013.01); *A61M 2025/0046* (2013.01); *A61M 2025/0681* (2013.01)

(58) Field of Classification Search
CPC .. A61M 2025/0681; A61 2025/0004; A61M 2025/0042; A61F 2/962
See application file for complete search history.

(56) References Cited

U.S. PATENT DOCUMENTS

| | | | |
|---|---|---|---|
| 5,765,682 A | | 6/1998 | Bley et al. |
| 5,830,217 A | | 11/1998 | Ryan |
| 5,964,261 A | * | 10/1999 | Neuenfeldt ........... A61F 2/0095 141/100 |
| 6,110,164 A | * | 8/2000 | Vidlund .............. A61M 25/005 604/524 |
| 7,651,488 B2 | | 1/2010 | Malisch |
| 8,109,908 B1 | | 2/2012 | Kraus et al. |
| 2004/0147877 A1 | | 7/2004 | Heuser |
| 2004/0256264 A1 | | 12/2004 | Israelsson et al. |
| 2005/0165379 A1 | | 7/2005 | Mawad |
| 2008/0177249 A1 | | 7/2008 | Heuser et al. |
| 2008/0228168 A1 | * | 9/2008 | Mittermeyer ........... A61L 29/14 604/525 |
| 2010/0160863 A1 | * | 6/2010 | Heuser .............. A61M 25/0662 604/164.1 |
| 2011/0160385 A1 | | 6/2011 | Fujisawa et al. |
| 2012/0071825 A1 | | 3/2012 | Cisko |
| 2012/0179144 A1 | | 7/2012 | Carleo |

FOREIGN PATENT DOCUMENTS

| | | |
|---|---|---|
| EP | 1575642 | 9/2005 |
| WO | WO96/27405 | 9/1996 |
| WO | WO 98/20812 A1 | 5/1998 |
| WO | WO01/07231 | 2/2001 |
| WO | WO 2005/014055 A2 | 2/2005 |
| WO | WO 2006/113856 A1 | 10/2006 |
| WO | WO 2007/120109 A1 | 10/2007 |
| WO | WO 2013/009520 A1 | 1/2013 |

OTHER PUBLICATIONS

Response to Examination Report dated Jan. 25, 2016 for GB1406501.5, 12 pgs.
Examination Report dated Feb. 11, 2016 for BG1406501.5, 2 pgs.
Examination Report for GB Application No. 1406501.5 dated Jul. 31, 2015, 3 pages.
Extended Search Report for EP Application No. 15 27 5082 dated Aug. 12, 2015, 14 pages.
Search and Examination Report for GB1406501.5 dated Oct. 24, 2014, 3 pgs.
Response to Search and Examination Report for GB1406501.5 dated Jan. 14, 2015, 17 pgs.

* cited by examiner

INTRODUCER ASSEMBLY AND PROTECTIVE SLEEVE THEREFOR

CROSS-REFERENCE TO RELATED APPLICATIONS

This application claims priority to GB application no. 1406501.5, filed Apr. 10, 2014, titled "INTRODUCER ASSEMBLY AND PROTECTIVE SLEEVE THEREFOR," the contents of which are incorporated herein by reference.

TECHNICAL FIELD

The present invention relates to an introducer assembly and to a protection sleeve, as well as to a method of deploying an introducer assembly, particularly useful for delicate or sensitive vessels such as the cerebral vessels.

BACKGROUND ART

There is increasing research and development into devices and methods for endoluminal treatment of or in small vessels, particularly the cerebral vessels. Such treatments can avoid the necessity for open surgical procedures, which can be traumatic, involve significant patient risk and require lengthy hospitalisation and recovery times. There are many treatments which can be performed on such vessels by endoluminal procedures, including just as examples, treatment of aneurysms, opening of vessels, implantation of filters, administration of medicaments, as well as delivery of diagnostic tools.

Small vessels, especially cerebral vessels, are particularly sensitive and as a result are prone to going into spasm should they be traumatised in any way. When a vessel begins to spasm it can close, preventing further movement of any endoluminal medical assembly in the vessel. Vessel spasm can occur when the vessels are touched by a hard substance, such as a part of an introducer assembly. It is not always practicable to make such assemblies of a soft material as they need to have a certain rigidity in order to have adequate pushability through a patient's vasculature and also to protect the components of the assembly. There have been suggestions as to how to soften such assemblies, but often this is after their implantation into a patient, and thus after they have been pushed through the patient's vasculature. Such solutions to not avoid the risk of causing vessel spasm.

As a result, and in order to maintain adequate pushability of the assembly, it has been known to limit the size of the introducer assemblies, so that they are significantly smaller in diameter than the diameter of the vessel. However, such diameter restriction limits the size of devices which can be introduced into these vessels and can limit the range of treatments or of diagnosis which can be performed.

Examples of prior art medical catheters and introducer assemblies can be found in US-2004/0059290, U.S. Pat. No. 4,976,703, U.S. Pat. No. 4,790,817, U.S. Pat. No. 7,651,488, US-2008/0228168 and WO-96/27405, the contents of which are incorporated by reference.

SUMMARY

The present invention seeks to provide apparatus and a method for more effective treatment within small and sensitive patient vessels.

According to an aspect of the present invention, there is provided an introducer assembly including: at least one introducer element of elongate tubular form and having an outer diameter, a protective sleeve of absorbable hydrophilic material, the protective sleeve having an internal diameter larger than the outer diameter of the at least one introducer element such that the introducer element is disposable within the protective sleeve.

The teachings herein provide a protective sleeve of an absorbable, in practice wettable, hydrophilic material which can be deployed in a patient's vessel so as to protect the vessel from damage or trauma caused by the deployment of an introducer assembly. The protective sleeve acts as a barrier or shield between the introducer assembly and the vessel wall. The material is able to be wetted prior to introduction into the sensitive vessels, for instance prior to introduction into the patient or in the course of endoluminal deployment through larger vessels, such that the sleeve is impregnated with liquid, making it very soft, enabling it to act as a cushion which protects the delicate vessels during the insertion of an introducer assembly. It will be appreciated that the introducer assembly could be of a conventional form, that is to have a medical device carrier, a sheath covering the medical device and carrier and other components of the introducer assembly. The protective sleeve therefore allows the use of conventional introducer assemblies while protecting the vessel walls.

Not only does the protective sleeve prevent trauma which can be caused by use of conventional introducer assemblies but it also enables the use of larger diameter introducer assemblies, that is assemblies having an outer diameter at their distal end closer to the inner diameter of the vessel in which the distal end is in use to be positioned. This enables the use of tools and medical devices having larger pre-deployment diameters, for instance larger tools or medical devices which have lower deployment compressibility, for example.

The introducer element is typically in the form of a catheter. The assembly may include at least one of: a medical device, a treatment tool and a diagnostic tool carried in the introducer element.

In the preferred embodiment, the protective sleeve is of a wettable hydrophilic material, such as a hydrogel polymer, preferably silicone hydrogel. Such materials are very soft when wet, that is when impregnated with fluid, and can be positioned against the walls of delicate vessels, such as cerebral vessels, without causing trauma or injury to the wall tissue.

Advantageously, the protective sleeve is a single layer of material. In an embodiment, the protective sleeve is of a material having a uniform wall thickness throughout the operative length of the protective sleeve.

It is preferred that the protective sleeve has a wall thickness of no more than 15% of its outer diameter. The protective sleeve may have an outer diameter of no more than around 2 millimeters.

In some embodiments, the protective sleeve includes a strengthening coil disposed therewithin. For example, the strengthening coil may be formed of spaced coil turns, wherein the spacing of the coil turns varies along a length of the protective sleeve. Advantageously, the spacing of the coil turns is greater at a distal end of the protective sleeve relative to a proximal end thereof. The spacing of the coil turns may be arranged in at least three sets, with a first set of relatively wide turn spacing at the distal end of the protective sleeve, a second set of coil turns of intermediate coil spacing adjacent the distal end of the protective sleeve and a third set of relatively tight coil spacing at the proximal end thereof.

In some embodiments, the protective sleeve includes a strengthening frame disposed therewithin. The strengthening frame may include a plurality of transversally disposed frame structures coupled together in longitudinally spaced relation by a flexible connector. Advantageously, the transversally disposed frame structures are rounded open frame petals. The flexible connector can be one of a rod and a wire.

The protective sleeve may be deployed in a preliminary procedure, prior to deployment of an introducer element, medical or diagnostic tool, for example.

According to another aspect of the present invention, there is provided a protective sleeve for implantation into the vasculature of a patient, the sleeve being of absorbable hydrophilic material and having a length, the sleeve including a strengthening member disposed substantially along the entire length thereof.

The strengthening sleeve may have any or all of the characteristics disclosed herein.

According to another aspect of the present invention, there is provided an assembly including: a casing and a protective sleeve for implantation in the vasculature of a patient, the protective sleeve being usable with an endoluminal introducer assembly and being of absorbable hydrophilic material; the protective sleeve being stored in the casing substantially immersed in an impregnation liquid, the casing being sealed in fluid tight manner.

According to another aspect of the present invention, there is provided a method of deploying an introducer element in the vasculature of a patient including the steps of: inserting into the vasculature of a patient a protective sleeve of absorbable hydrophilic material, the protective sleeve having been wetted prior to insertion into the patient; a distal end of the protective sleeve being disposed adjacent a site of the patient's vasculature where treatment is to be carried out; subsequently deploying through the protective sleeve an introducer element of elongate tubular form, whereby the protective sleeve acts to protect the patient's vasculature from contact with the introducer element substantially up to the site of treatment.

Advantageously, a protective sleeve is chosen having an outer diameter at its distal end close to an inner diameter of the vessel at which the distal end is in use positioned.

The sleeve may be positioned first, with the introducer element then fed through the sleeve. In another embodiment, the introducer element may be at least partially located within the protective sleeve and the two elements fed endoluminally through the patient's vasculature up to the treatment site, whereupon the introducer element is then pushed out of the distal end of the sleeve to perform the medical procedure.

Other features and advantages are disclosed below.

BRIEF DESCRIPTION OF THE DRAWINGS

Embodiments of the present invention are described below, by way of example only, with reference to the accompanying drawings, in which.

DISCLOSURE OF THE PREFERRED EMBODIMENTS

The teachings herein are directed to a protective sleeve which can be used in addition to the components of a conventional introducer assembly and which acts as a barrier between the introducer assembly and the walls of the vessel. The protective sleeve is particularly useful in the deployment of an introducer assembly in delicate vessels, such as the cerebral vessels.

Figure 1:
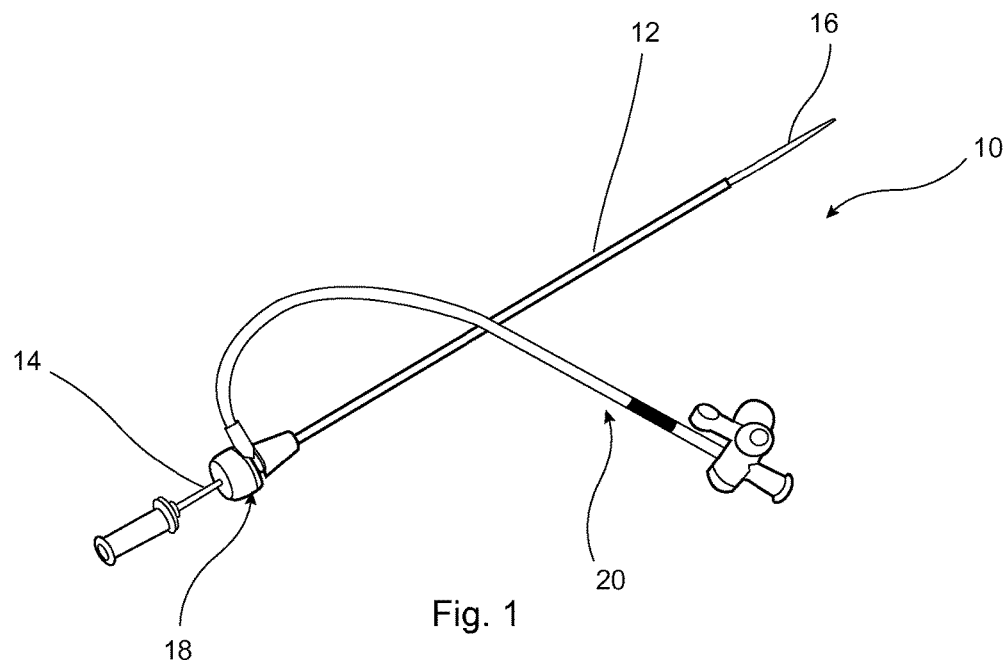
FIG. 1 is a perspective view of an example of conventional introducer assembly.

Referring first to FIG. 1, this shows in general format the principal components of a standard introducer assembly 10. It is to be understood that the teachings herein are not limited to any particular form of introducer assembly and that FIG. 1 shows an example solely for the purposes of explaining the nature of the teachings in the present application.

The assembly 10 of FIG. 1 includes an introducer catheter or sheath 12, of conventional form, within which there is disposed an inner elongate element 14, which may be a catheter, push rod, treatment tool, diagnostic tool or the like. The catheter or sheath 12 in practice covers the internal components of the assembly 10 and can be of a type commonly used with conventional introducer assemblies. In this particular example, the inner element 14 is an inner catheter. At a distal end of the assembly 10 there is provided a dilator tip 16, while at a proximal end there is provided a handle and valve unit 18. The unit 18 typically includes a flushing chamber coupled to a tube 20, designed to be coupled in turn to a source of flushing fluid such as saline solution. The assembly 10 is provided with a plurality of connectors of conventional type, which are therefore not described herein.

The assembly 10, and in particular the catheter 12 and elongate element 14, are flexible so as to be able to follow the tortuous path through a patient's vasculature. It is also important for the assembly 10 to have a certain longitudinal strength so that it can be pushed through the vasculature. Specifically, the catheter 12 and elongate element 14 should not be unduly soft as this would adversely affect their ability to be deployed endoluminally from a remote percutaneous entry point. These are characteristics with which the person skilled in the art will be very familiar.

Figure 2:
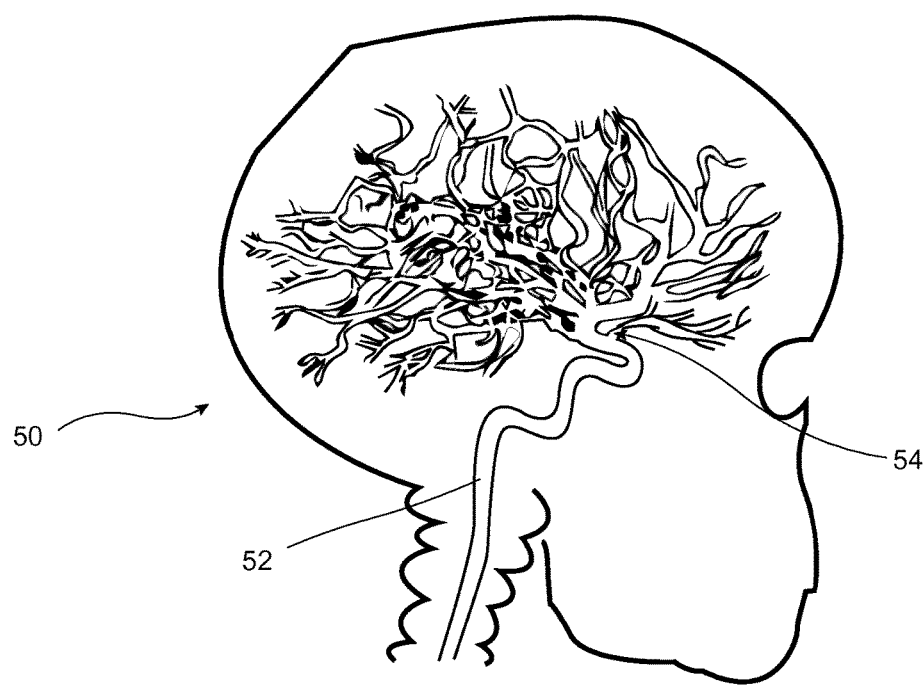
FIG. 2 is a schematic diagram the cerebral arterial system.

Referring now to FIG. 2, this shows in schematic form the cerebral arteries of a human skull 50. The basilar artery 52 extends through the person's neck and branches into the posterior cerebral arteries 54 and thereafter into a network of smaller arteries throughout the brain. As can be seen in FIG. 2 and as will be familiar to the person skilled in the art, the cerebral arteries and veins are particularly tortuous, as well as being very delicate. When contacted by a hard object these vessels tend to spasm and close, which will block any further passage of a device such as an introducer assembly 10 through the vessels. As described above, attempts to avoid vessel spasm have included making the introducer assembly, particularly the distal end, very soft but this results in a loss of pushability of the device through the vasculature. Other attempts have sought to reduce the diameter of the introducer assembly 10, which will assist in its pushability and also enable it to be more flexible, however, with a reduction in the volume within the introducer assembly limiting the size of any medical device or treatment or diagnostic tool carried in the assembly.

Figure 3:
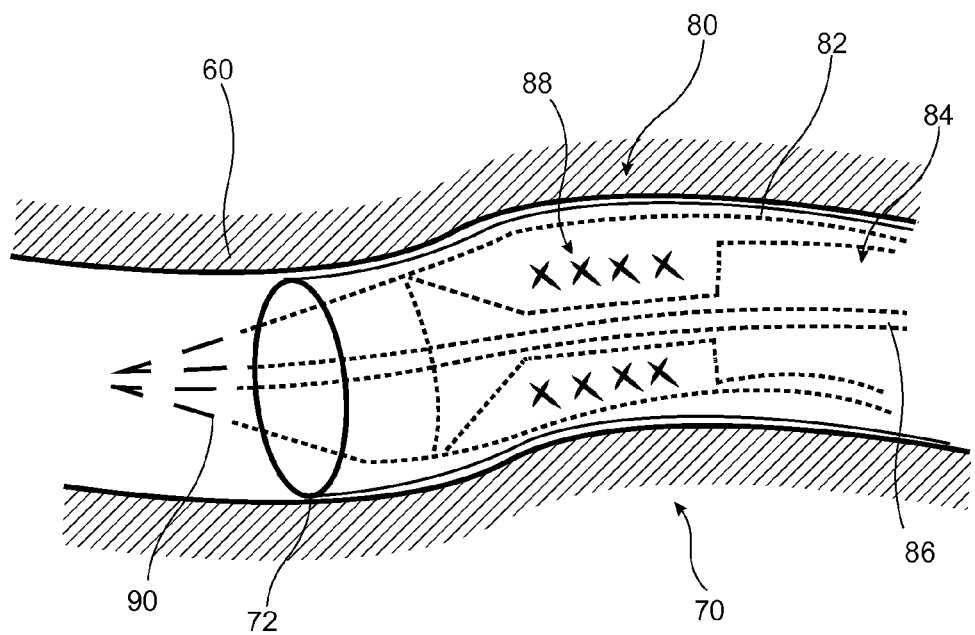
FIG. 3 is a schematic diagram in partial cross-section of the distal end of an embodiment of apparatus according to the teachings herein.

Referring now to FIG. 3, this shows a section of a vessel 60, which may be a cerebral vessel of the type shown in FIG.

2, and the distal end of a preferred embodiment of apparatus 70 according to the teachings herein. The apparatus 70 includes a protective sleeve 72 made of absorbable hydrophilic material, typically a wettable hydrophilic material. It is preferred that the sleeve 72 is made of a hydrogel polymer, such as a silicone hydrogel. Silicone hydrogels have both the very high oxygen permeability of silicone and the comfort and clinical performance of conventional hydrogels. They are, therefore, considered particularly useful for the protective sleeve 72.

As can be seen in FIG. 3, the protective sleeve 72 is preferably selected to have an outer diameter only slightly smaller than the inner diameter of the vessel 60 in which it is intended to be deployed, specifically at the treatment site. The protective sleeve 72 is pre-wetted prior to introduction in a patient, for example by being soaked in water or a solution such as saline solution. Pre-wetting causes the sleeve 72 to be impregnated with the liquid, which will cause it to soften significantly and attain a state in which the sleeve 72 itself will not cause any trauma to the vessel wall. Wetting will typically cause the sleeve 72 to expand from its dry state.

It is preferred that the sleeve 72 is supplied in a pre-wetted condition, typically by being stored in the impregnation fluid in a liquid-proof sealed and sterilised container. The sleeve 72 will therefore already be in its operative condition without it being necessary to carry out any wetting process prior to use of the sleeve 72.

The sleeve of all the embodiments disclosed herein can have the above mentioned characteristics.

The assembly 70 also includes, when considered in its entirety, an introducer element 80, which may be similar to the introducer assembly 10 of FIG. 1. In this example, the introducer element 80 includes a sheath or catheter 82, of a type conventionally used in introducer assemblies, and an elongate pusher rod 84 having a lumen 86 therein and supporting an implantable medical device 88, in this example a stent. A dilator 90 is located at the distal end of the pusher element 84 and extends beyond the distal end of the catheter 82. As will be apparent from FIG. 3, the introducer element 80 is held within the protective sleeve 72, such that the sleeve 72 acts as a barrier between the introducer element 80 and the walls of the vessel 60. As a result, any rigidity of the introducer element 80 or any sharp edges or surfaces which it may have are buffered by the protective sleeve 72.

During deployment of the introducer element 80, and in this example during deployment of the stent 88 carried by the introducer element, it will be appreciated that the distal end of the assembly will be pushed out of the distal end of the sleeve 72. It is preferred that this is carried out with the distal end of the introducer element 80 generally aligned with the centre of the vessel 60.

As explained above, the provision of the protective sleeve 72 enables the use of stiffer and/or greater diameter introducer elements 80 as a result of the cushioning effect of the protective sleeve 72. The introducer element 80 can have an outer diameter approaching the inner diameter of the vessel 60 at the treatment site.

It is preferred that the protective sleeve 72 has a thin wall, for example having a wall thickness of no more than around 15% of its outer diameter. In some embodiments the protective sleeve 72 may have an outer diameter of than no more than around 2 mm. The protective sleeve 72 may be made of a single material having a wall of a single layer. It is not excluded, though, that the protective sleeve 72 may have a wall made of a plurality of layers, optionally having different characteristics. It is also envisaged that in some embodiments only a part of the sleeve 72, typically the outermost layer, is made of a wettable, or absorbable, hydrophilic material. This is, however, not a preferred embodiment.

In its simplest form the protective sleeve 72 is a single layer of material and is therefore very soft and compliant. A sleeve of this nature can be introduced into the vasculature of a patient over a small catheter, the latter being guided over a guide wire of known type. For this purpose, the catheter can have an outer diameter which is only a fraction of the diameter of the sleeve and substantially less than the diameter of the vessel.

Figure 4:
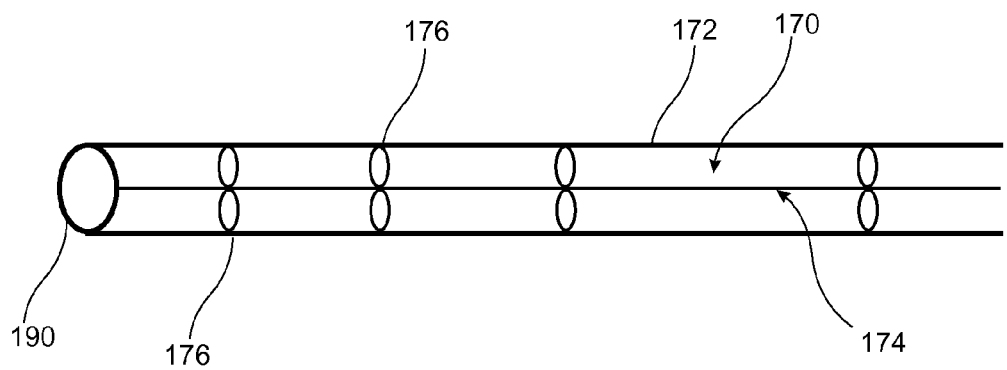
FIG. 4 is a side elevational view of an embodiment of protective sleeve according to the teachings herein.
Figure 5:
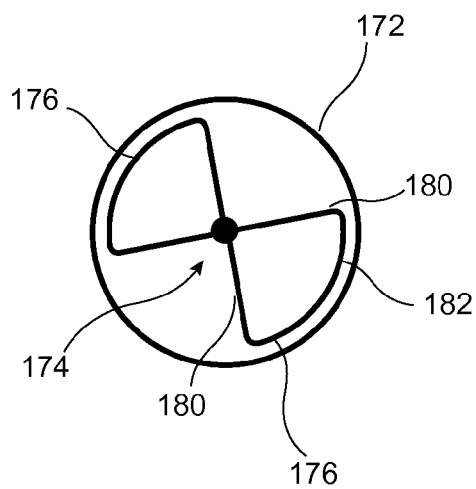
FIG. 5 is an end view of the embodiment of protective sleeve of FIG. 4.
Figure 6:
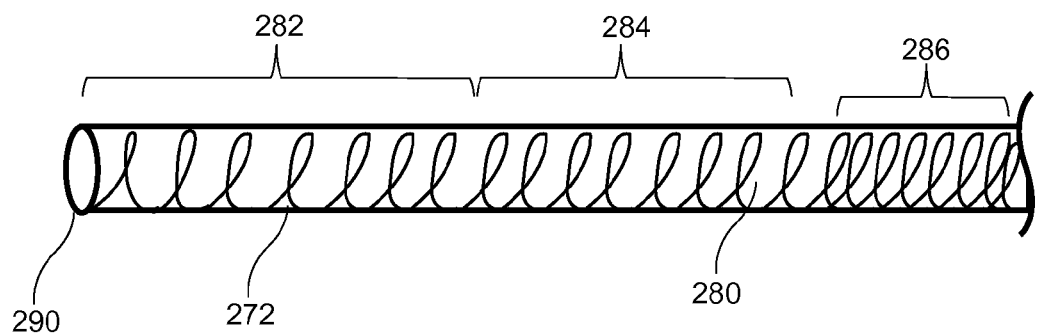
FIG. 6 is a side elevational view of another embodiment of protective sleeve according to the teachings herein.

FIGS. 4 to 6 show two embodiments of protective sleeve 72 which are provided with different forms of strengthening elements therein. Referring first to FIGS. 4 and 5, these show an embodiment of protective sleeve 172 having the same structure and made of the same materials as the sleeve 72 described above. Disposed within the sleeve 172 is an insert 170 which includes a rod or wire 174 extending through the sleeve 172. Disposed at spaced intervals on the wire 174 is a plurality of sets of winged spacer elements 176, which may have a form as shown in FIG. 5 and which could be described as petals. Each element 176, in this embodiment, subtends a part of a circle and is formed by a wire having two radially extending components 180 coupled to respective ends of a part-circular portion 182. In this example there are provided two winged spacer elements 176 in each set, each element 176 extending over about a quarter of the circumference of the protective sleeve 172. In other embodiments a different number of spacer elements may be provided, as well as spacer elements having different relative dimensions and shapes.

The insert 170 may be fixed to the sleeve 172, for example by fixing the arc elements 182 to the inner wall of the sleeve 172 or by embedding these in the wall of the sleeve 172. In other embodiments the insert 170 may be separate from the sleeve 172 and removable therefrom once the sleeve 172 has been positioned correctly within the patient's vasculature.

The support structure shown in FIGS. 4 and 5 is particularly useful when the protective sleeve 176 is intended to act also as an aspiration catheter, for example, to remove debris from a vessel. The petals 176 act to keep the sleeve 172 open during aspiration. This application can be useful, for example, for collecting debris created during an angioplasty procedure.

The pairs of winged spacer elements 176 in the embodiment of FIGS. 4 and 5 are spaced from one another along the length of the strengthening sleeve 172 by differing amounts. Specifically, the spacing between the pairs of winged elements 176 reduces towards the distal end 190 of the protective sleeve 172, so as to provide greater opening force of the sleeve 172 at its distal end. This can be advantageous when the protective sleeve 172 is used as an aspiration catheter, for example. In other embodiments, the spacing between pairs of winged spacer elements 176 may get greater towards the distal end of the protective sleeve 172, so as to give this increased flexibility at its distal end.

The spacer elements 176 may be made of any suitable material, including spring steel, shape memory alloy such as Nitinol or the like. The rod or wire 174 may be made of the same materials. It is not necessary for the wire or rod 174 to be made of a shape memory material, though, even in embodiments where the petals 176 are.

Referring now to FIG. 6, there is shown another embodiment of protective sleeve 272, which is provided with a strengthening coil 280, which may be provided at the inner surface of the protective sleeve 272 or embedded within the wall of the sleeve 272. The coil 280 may be made of any suitable material, including spring steel, shape memory alloy such as Nitinol or the like. In this embodiment, the strengthening coil 280 has coil turns of varying spacing, in this example a greater spacing between adjacent coil turns in zone 282 close to the distal end 290 of the protective sleeve 272. In an intermediate zone 284, the coil may have a slightly tighter coil spacing so as to give the protective sleeve 272 slightly less flexibility, whereas towards the proximal end of the protective sleeve 272, in zone 286, the coil 280 may have a tight turn spacing so as to give this increased pushability to assist in feeding the sleeve through the vasculature of a patient.

The sleeve 272 could be used in the assembly shown in FIG. 3 and in the same way.

The preferred embodiments of protective sleeve can be used for cerebral applications. For such applications, the sleeve may have an outer diameter of around 2 mm for feeding into vessels having a diameter as small as around 3 mm or less. The catheter tip may have a diameter of around 0.4 mm and a shaft of around 1 mm, although the catheter shaft could have a diameter up to just less than the inner diameter of the sleeve.

One method of deploying an introducer element in the vasculature of a patient includes the following steps. The protective sleeve 72, 172, 272, is inserted into the vasculature of the patient, the protective sleeve already being in a wetted state prior to insertion into the patient. The distal end 290 of the protective sleeve is positioned adjacent a site of the patient's vasculature where treatment is to be carried out. Subsequently, an introducer element 70 of elongate tubular form is deployed through the protective sleeve, whereby the protective sleeve 72, 172, 272 acts to protect the patient's vasculature from contact with the introducer element 70 up to the site of treatment.

Thus, the protective sleeve 72, 172, 272 is used in a preliminary procedure prior to deployment of the introducer element.

Advantageously, the protective sleeve 72, 172, 272 has an outer diameter at its distal end close to an inner diameter of the vessel at which the distal end 290 is disposed. In some embodiments, the protective sleeve 72, 172, 272 is chosen to have an outer diameter at its distal end at least 65% of the inner diameter of the vessel at which the distal end is disposed.

The introducer element may carry an implantable medical device, in other embodiments may be a treatment tool or a diagnostic tool.

In this method, as explained above, the protective sleeve could be provided with the support or strengthening elements shown in any of FIGS. 4 to 6.

Another method involves locating the introducer element into the sleeve 72, 172, 272 prior to insertion into the patient, such that the sleeve 72, 172, 272 is deployed simultaneously with the introducer element.

It is preferred that the protective sleeve 72, 172, 272 is supplied to the end user, typically the hospital, in a pre-wetted condition. For this purpose, it is preferred that the sleeve 72, 172, 272 is housed in a liquid tight transport and storage container filled with impregnation fluid, for example saline solution. The sleeve 72, 172, 272 will therefore be ready for immediate use in the operating theatre, in its impregnated state.

The sleeve 72, 172, 272 may be of a single layer of material and/or may have a uniform wall thickness throughout its operative length.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The disclosure in the abstract accompanying this application are incorporated herein by reference.

I claim:

1. A method of deploying an introducer element in the vasculature of a patient including the steps of:
   inserting into the vasculature of the patient a protective sleeve of absorbable hydrophilic material, the protective sleeve having been wetted prior to insertion into the patient; a distal end of the protective sleeve being disposed adjacent a site of the patient's vasculature where treatment is to be carried out;
   subsequently deploying through the protective sleeve an introducer element of elongate tubular form, whereby the protective sleeve acts to protect the patient's vasculature from contact with the introducer element up to the site of treatment.

2. The method of claim 1, wherein the introducer element of elongate tubular form is a sheath and wherein at least one of: a medical device, a treatment tool and a diagnostic tool is carried in the introducer element of elongate tubular form.

3. The method of claim 1, wherein the protective sleeve has a wall which consists essentially of said absorbable hydrophilic material.

4. The method of claim 1, wherein the protective sleeve has a length which is at least 90% of a length of the introducer element.

5. The method of claim 1, wherein the protective sleeve comprises a wettable hydrophilic material.

6. The method of claim 1, wherein the protective sleeve comprises a hydrogel polymer.

7. The method of claim 1, wherein the protective sleeve comprises silicone hydrogel.

8. The method of claim 1, wherein the protective sleeve is of a single layer of material.

9. The method of claim 1, wherein the protective sleeve is of a material having a uniform wall thickness throughout an operative length of the protective sleeve.

10. The method of claim 1, wherein the protective sleeve has a wall thickness of no more than 15% of its outer diameter.

11. The method of claim 1, wherein the protective sleeve has an outer diameter of no more than around 2 millimeters.

12. The method of claim 1, wherein the protective sleeve includes a strengthening coil disposed therewithin.

13. The method of claim 12, wherein the strengthening coil is formed of spaced coil turns, wherein the spacing of the coil turns varies along a length of the protective sleeve.

14. The method of claim 13, wherein the spacing of the coil turns is greater at a distal end of the protective sleeve relative to a proximal end thereof.

15. The method of claim 14, wherein the spacing of the coil turns is arranged in at least three sets, with a first set of relatively wide turn spacing at the distal end of the protective sleeve, a second set of coil turns of intermediate coil spacing adjacent the distal end of the protective sleeve and a third set of relatively tight coil spacing at the proximal end thereof.

16. The method of claim 1, wherein the protective sleeve includes a strengthening frame disposed therewithin.

17. The method of claim 16, wherein the strengthening frame includes a plurality of sets of transversally disposed frame structures coupled together in longitudinally spaced relation by a flexible connector.

18. The method of claim 17, wherein the transversally disposed frame structures are rounded open frame petals.

19. A method according to claim 1, wherein the protective sleeve has an outer diameter at its distal end close to an inner diameter of the vessel at which the distal end is disposed.

20. A method according to claim 19, wherein the protective sleeve has an outer diameter at its distal end at least 65% of the inner diameter of the vessel at which the distal end is disposed.

21. A method according to claim 1, comprising the step of deploying a medical device, a treatment tool or a diagnostic tool through the introducer element.

* * * * *